United States Patent [19]

Richman

[11] 4,383,905
[45] May 17, 1983

[54] SYSTEM FOR HYDRODYNAMIC COMPENSATION FOR ELECTROPHORESIS CRESCENT DISTORTION

[75] Inventor: David W. Richman, St. Louis County, Mo.

[73] Assignee: McDonnell Douglas Corporation, St. Louis, Mo.

[21] Appl. No.: 306,510

[22] Filed: Sep. 28, 1981

Related U.S. Application Data

[62] Division of Ser. No. 178,833, Aug. 15, 1980, Pat. No. 4,309,268.

[51] Int. Cl.³ .................... G01N 27/26; G01N 27/40
[52] U.S. Cl. .................................................. 204/180 R
[58] Field of Search ............ 204/180 R, 180 G, 299 R, 204/301

[56] References Cited

U.S. PATENT DOCUMENTS

| | | | |
|---|---|---|---|
| 3,450,624 | 6/1969 | Natelson | 204/180 G |
| 3,498,905 | 3/1970 | Strickler | 204/180 R |
| 3,509,035 | 4/1970 | Heubner | 204/180 R |
| 3,519,549 | 7/1970 | Grassmann et al. | 204/180 R |
| 3,655,541 | 4/1972 | Strickler | 204/180 R |

Primary Examiner—John F. Niebling
Attorney, Agent, or Firm—Gregory A. Cone; Walter J. Jason; Donald L. Royer

[57] ABSTRACT

Crescent distortion of output samples collected during a continuous free flow electrophoresis separation process is reduced by providing means with the electrophoresis chamber whereby lateral flow across the chamber may be controllably varied to introduce beneficial hydrodynamic compensation effects to minimize distortion of the sample streams within the electrophoresis chamber.

5 Claims, 10 Drawing Figures

SYSTEM FOR HYDRODYNAMIC COMPENSATION FOR ELECTROPHORESIS CRESCENT DISTORTION

This is a division, of application Ser. No. 178,833, filed Aug. 15, 1980, now U.S. Pat. No. 4,309,268.

BACKGROUND OF THE INVENTION

1. Field of the Invention

The present invention relates to an apparatus and a method for performing a continuous free flow electrophoresis process. More particularly, the present invention relates to an apparatus and a method for performing a continuous free flow electrophoresis procedure in which crescent distortion of the samples is reduced by providing for means to introduce hydrodynamic compensation within the electrophoresis chamber to minimize the crescent distortion effects.

2. Description of the Prior Art

Electrophoresis, in general, in the phenomenon of the migration of charged particles or ions in a liquid carrier medium under the influence of an electric field. This phenomenon can be used to separate small particles which, by reason of different surface chemical properties, exhibit different concentrations of surface charge in the given medium. Under the influence of the electrical field, the electrophoretic mobilities of the various classes of charged particles in the carrier medium will be different. A sample continuously introduced at some point into the sheet of liquid carrier medium (buffer) flows in a narrow band in the absence of a potential gradient; however, when the potential gradient is applied to the sheet of buffer, the sample particles are separated under the influence of the electrical field into various particle groups or components depending upon the electrophoretic mobility of the respective particles, the strength of the field, and the length of time that the particles remain in the field. Particles of similar mobility are concentrated in distinctive zones or bands which fan out from the point of sample introduction.

The present invention relates in particular to free flow continuous electrophoresis in which a buffer solution is made to flow freely in a uniform film or sheet through a chamber defined by two parallel enlongate plates. A sample is introduced into the buffer sheet at some point, and an electric potential gradient is applied across this flowing sheet perpendicular to the direction of buffer flow. The individual components within each sample then separate into narrow bands depending upon their respective electrophoretic mobilities and can be collected from the outlet end of the electrophoresis chamber through one or more of a plurality of small tubes disposed along a collection manifold at the outlet of the chamber.

However, almost invariably, a number of factors inherent in the electrophoresis process combine to introduce distortion into the various individually deflected sample streams. This distortion, when examined in a cross section perpendicular to the flow within the chamber, assumes a crescent shape and is, therefore, most commonly referred to as "crescent distortion." The only known method for compensation for the crescent distortion effect is to employ appropriate coatings to the interior chamber walls such that the zeta potential of these coatings will induce an electro-osmotic flow velocity along the walls of the chamber which is approximately equal in magnitude but opposite in direction to the electrophoretic velocity of the individual sample which is desired to be collected. A publication by Allen Strickler and Terry Sacks in "Preparative Biochemistry," Volume III, No. 3 (1973), pages 269 to 277, teaches that crescent shaped deformations of the flow cross section of a given fraction, resulting from the velocity profile of the buffer stream, can be compensated by appropriate setting of the zeta potential of the separation chamber walls so that, for this fraction, the sample stream can be given a well defined cross section transverse to the flow direction, and thus optimum separation efficiency can be obtained. There is also a U.S. patent to Allen Strickler, U.S. Pat. No. 3,758,395 (Sept. 11, 1973) entitled "Resolution And Symmetry Control In Continuous Free Flow Electrophoresis" which teaches a method for crescent distortion compensation by adjusting the effective zeta potential of the chamber walls to optimize resolution by providing each of the walls of the apparatus with areas spaced along the length thereof having different zeta potentials and by either mechanically or electrically adjusting the relative electro-osmotic contribution of each area. Other U.S. patents involving continuous flow electrophoresis devices include U.S. Pat. No. 3,458,427 (July 29, 1969) to Strickler, U.S. Pat. No. 3,663,395 (May 16, 1972) to Strickler, U.S. Pat. No. 3,655,541 (Apr. 11, 1972) to Strickler, and U.S. Pat. No. 4,061,560 (Dec. 6, 1977) to Hannig, et al.

U.S. Pat. No. 3,458,427 to Strickler (July 29, 1969) bears a superficial resemblance to the method and apparatus of the present invention and for this reason bears further comment. This patent discloses a continuous free flow electrophoresis apparatus which includes means for varying the discharge flow rate of one portion of the flowing electrolyte sheet carrying the component bands with respect to the discharge flow rate of a second portion of the electrolyte sheet to cause a shift in the electrolyte sheet in a lateral direction to bring the desired component band into alignment with a collecting device. The essence of this device is then to shift the entire flow within the chamber, without compensating whatsoever for the distortion effects, in order that the single band of particulate material desired to be collected can be shifted to a single, fixed collection port for removal from the electrophoresis chamber. Apparently the phenomenon of crescent distortion was either unknown or ignored at the time of this patent, since no mention of the phenomenon is made in this patent, nor is any method proposed for its compensation.

As was mentioned hereinbefore, the only method heretofore disclosed for the compensation of the crescent distortion effect in an electrophoresis procedure is to adjust the zeta potential of the walls of the electrophoresis chamber, thereby inducing an electro-osmotic flow velocity which will minimize the crescent distortion effect. However, this method is only effective for a sample of a specific electrophoretic mobility. Hence, if more than one sample stream is desired to be collected, each such stream having a necessarily different electrophoretic mobility, the crescent distortion may be minimized for one of the sample streams only, leaving the other sample streams subject to the effect of the crescent distortion phenomenon. Also, the methods proposed for adjusting the zeta potential of the chamber walls tend to be rather cumbersome and time consuming in their application, thereby limiting the use of the process to situations in which samples of only a relatively narrow range of mobilities will be separated.

Consequently, the flexibility of the various electrophoresis chambers with the zeta potential compensation feature of the prior art is severely compromised because such chambers cannot be quickly adapted to handle a variety of different samples wherein the samples for each separation differ more than minimally in the range of electrophoretic mobilities of their individual components.

SUMMARY OF THE INVENTION

In an apparatus for conducting a continuous free flow electrophoresis separation procedure wherein the apparatus comprises a lengthwise elongate, rectangular separation chamber defined by two elongate, spaced apart, parallel plates; two sides, an end comprising a collection manifold having a plurality of spaced apart collection tubes; an end comprising a buffer solution inlet manifold assembly; two buffer filled electrode chambers, each disposed adjacent to one of the sides of the chamber and separated therefrom by a membrane; and at least one sample inlet port located at or near the bottom of the chamber; crescent distortion for at least one of the individual components of a sample which is introduced into the buffer filled separation chamber is minimized by means whereby lateral flow within the separation chamber may be controllably varied across the chamber.

BRIEF DESCRIPTION OF THE DRAWINGS

FIG. 4 also illustrates the crescent distortion compensation effects of this invention when the hydrodynamic compensating flow is uniform across the chamber;

DETAILED DESCRIPTION OF THE INVENTION

A continuous free flow electrophoresis separation procedure is a process which finds application in separating out the various components of a sample stream composed of various different proteins, cells, or other particles, each such component having a particular surface electrical charge. The sample stream is introduced into a buffer filled electrophoresis chamber in which the buffer and the sample are continuously circulated from the inlet to the outlet end of the chamber. The buffer solution is designed to maintain the viability of samples over the course of the separation procedure. An electrical field is applied across the flow in the direction of the desired separation.

The basis for separation is electrophoresis or the motion of charged particles in an electrical field. This motion is a result of the force on the particles which is proportional to their charge and the electrical field strength. Under the influence of this force, the particles are rapidly accelerated in the direction of the electrical field to approach a terminal velocity limited by the force of the viscous drag on the particles. The various individual particles will, in general, have different lateral terminal velocities and will diverge into discrete bands composed of particles of the same terminal velocity as the samples progress along the length of the separation chamber towards the collection ports at the outlet end of the chamber. The characteristic used to quantify this effect is particle mobility, which is the velocity component in the direction of the electrical field divided by the electrical field strength. The distance that the particles travel in the direction of the electrical field is proportional to the residence time within the chamber. Hence, particles with higher terminal velocities will migrate further laterally under the influence of the electrical field.

Figure 1:
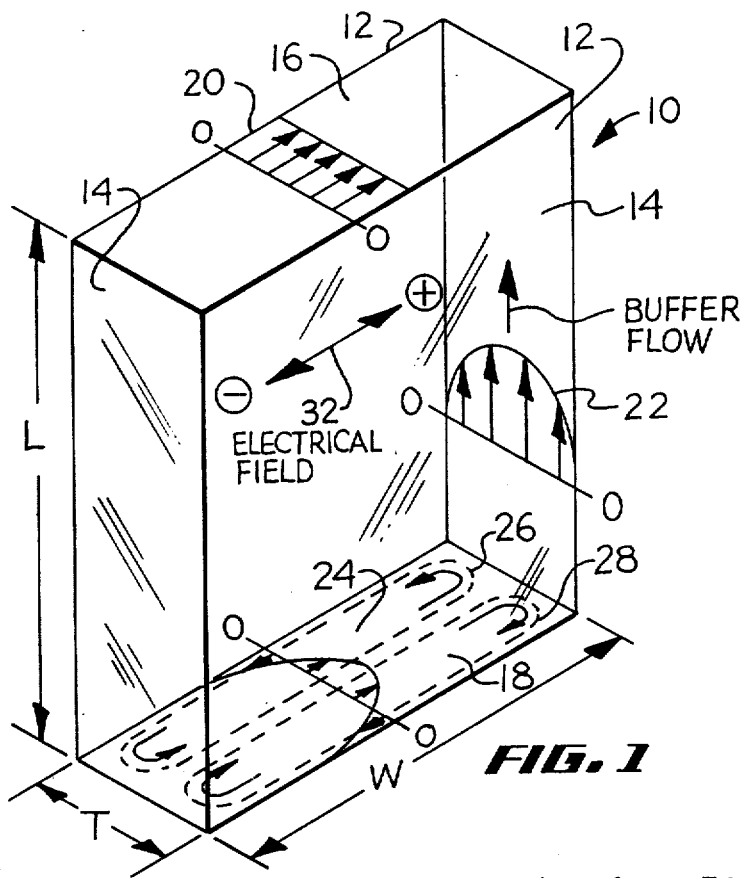
FIG. 1 illustrates the various flows within an electrophoresis chamber.
Figure 2:
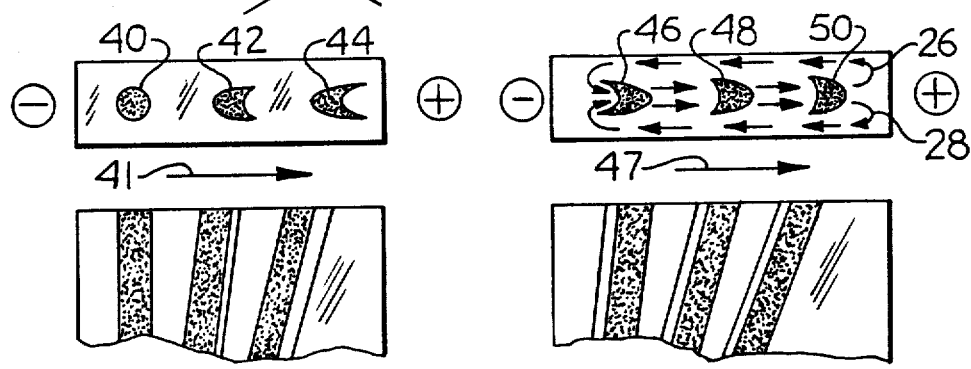
FIG. 2 illustrates the crescent distortion phenomenon in both horizontal and vertical sections through an electrophoresis chamber.
Figure 2:
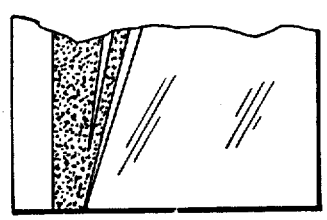

However, the electrophoretic force is not the only force acting upon the particles. Because of fluid friction within the chamber, the velocity of the buffer solution molecules is highest in a plane midway between the closely spaced front and back walls of the chamber and decreases to zero at the walls. Therefore, particles that enter the buffer stream closer to the walls will remain in the chamber for a longer period of time, causing an increased deflection compared to those particles in the same sample stream that are inlet closer to the center of the chamber. The fluid friction effects are seen in the velocity profile 22 of FIG. 1. The electrophoretic force vectors 20, however, are constant across the thickness of the electrophoresis chamber. When these two effects are superimposed, the crescent distortion phenomenon is produced such as that shown in FIG. 2. The sample stream 40 on the left of the chamber in FIG. 2 has a very low mobility 41 when compared with sample streams 42 and 44. FIG. 2 then illustrates the crescent distortion phenomenon only, which is a combination of the effects of both the electrophoretic and viscous forces upon the individual sample streams flowing through the buffer filled electrophoresis chamber.

Figure 3:
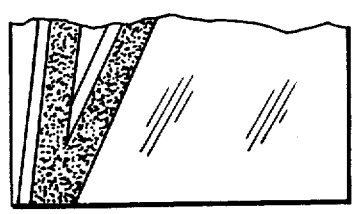
FIG. 3 illustrates the combination of crescent distortion and electro-osmotic circulation in both horizontal and vertical sections in an electrophresis chamber.

Electro-osmosis is another important distortion effect present within an electrophoresis chamber. Electro-osmosis is a circulation of the carrier buffer in a plane normal to the buffer flow that results from the interaction of the buffer, the electrical field, and the wall material, being dependent upon the potential differences between the wall and the buffer. If the wall is negatively charged, positive ions in the buffer are attracted by Coulomb forces. This causes the buffer solution very near the wall to have a positive charge differential relative to the bulk charge of the buffer and a resulting force differential in favor of migration toward the negatively charged electrode. The force differential is proportional to the zeta potential, a wall material characteristic, which is the potential difference between the surface of the double layer and the bulk of the solution. This force is in equilibrium with the shear force due to the large velocity gradient at the wall. Because the chamber ends are closed, the buffer migrating towards the negatively charged electrode must circulate back along the chamber center line. This creates two flow cells 26 and 28 as seen in FIGS. 1 and 3. The resulting velocity profile 24 of the electro-osmotic flow is parabolic since the boundary conditions are the same as in Poiseuille flow; that is, constant wall velocity and constant pressure across the chamber. In this case, however, the velocity near the wall is not zero and the integral of velocity across the chamber is zero to satisfy conservation of mass. For these boundary conditions, the chamber center line electro-osmotic velocity is one half the electro-osmotic velocity at the wall and in the opposite direction, with a zero velocity point being found at a distance about twenty percent of the chamber thickness from each of the walls. The electro-osmotic forces are often stronger than the electrophoresis forces and commonly produce a crescent distortion pattern such as that found in FIG. 3 with the electrical field as shown and the electrophoretic mobility 47 increasing towards the right of the chamber.

Figures 4, 5:
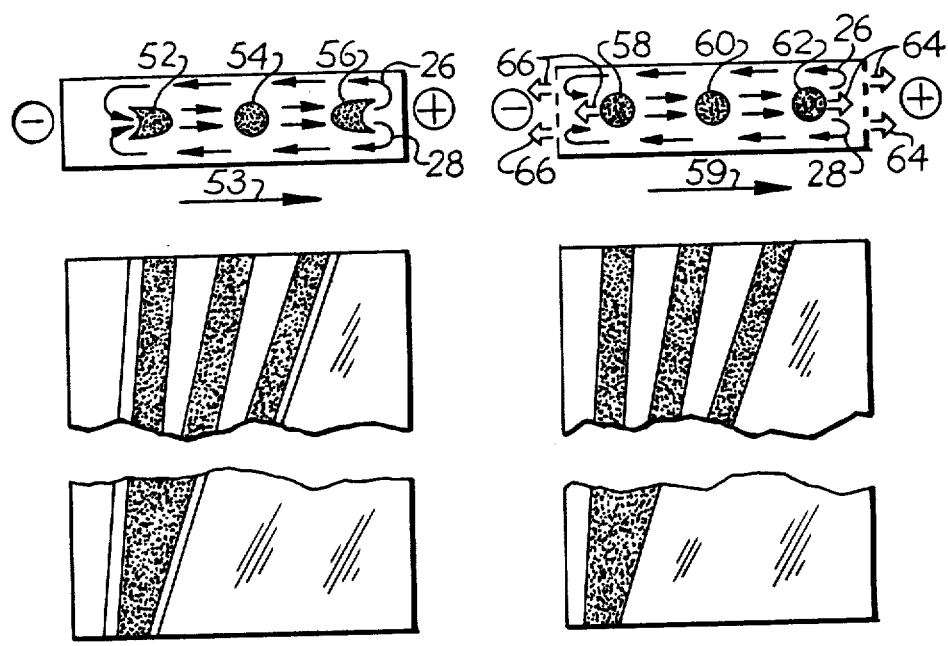
FIG. 4 illustrates a prior art method of crescent distortion compensation wherein, by adjusting the zeta potential of the chamber walls, crescent distortion for one of the components is minimized, being shown in both horizontal and vertical sections.
FIG. 5 illustrates the crescent distortion compensation effects of this invention when the hydrodynamic compensating flow is of an appropriate non-uniform variation across the chamber.

Conditions within the electrophoresis chamber can be structured, however, to produce a balanced condition wherein one of the component sample streams of a particular mobility can be made to display minimal crescent distortion. This condition is illustrated in FIG. 4. Sample stream 54 displays a circular cross section indicating that the electro-osmotic and electrophoretic forces are in balance for this particular sample stream. This condition occurs when the center line electro-osmotic velocity is in the same direction as the electrophoretic velocity and is optimized when the electro-osmotic wall velocity is the negative of the electrophoretic veocity. This condition has been achieved in the prior art by adjusting the zeta potential of the wall coatings in the electrophoresis chamber. However, as illustrated in FIG. 4, the minimization of crescent distortion is only effective for a sample stream of one particular mobility, leaving the crescent distortion phenomenon to affect the other different mobility sample streams 52 and 56 present in the chamber. The cross section of the sample on the left 52 is for particles of zero mobility. Here the electro-osmotic return flow causes the sample at the center line to advance farther in the direction of flow than parts of the sample closer to the walls. The cross section on the right 56 is for particles with twice the electrophoretic mobility of the particles in the center cross section 54. Here the electro-osmotic return flow is not large enough to compensate for the crescent distortion, thereby permitting the parts of the sample closer to the walls to undergo a larger deflection.

The condition of crescent distortion control for a sample stream of one particular mobility can be more easily effected using the system of this invention. In this case, the walls of the chamber can be made of any one material, which in turn results in an electro-osmotic flow of a particular magnitude. If the magnitude of this initial electro-osmotic flow does not result in the desired compensation, then an additional uniform lateral flow can be induced across the chamber by flowing buffer solution into the chamber uniformly along one membrane and having the same uniform flow of buffer solution out of the chamber at the other membrane.

The system of this invention, however, also compensates for crescent distortion for a range of mobilities rather than a single mobility, thereby resulting in multiple high resolution quality separations from a single electrophoretic process. This distinct improvement is gained in my invention by introducing controlled non-uniform distortion to the parallel chamber flow by a technique of hydrodynamic compensation. The hydrodynamic compensation is achieved by the addition of means for producing an adjustable lateral flow out through the sides of the electrophoresis chamber such that the forces tending to introduce crescent distortion to the fluid sample streams are counteracted and minimized.

One hydrodynamic compensation technique is to employ a porous membrane between the electrode chambers at each side of the electrophoresis chamber with means to adjust the flow across the porous membrane such that a net flow of buffer solution may be controllably maintained from the electrophoresis chamber into the electrode chamber. Each electrode chamber would have separate control means in order that the exact hydrodynamic compensation flows necessary to achieve uniform minimization of crescent distortion for the fluid sample streams could be produced for a variety of ranges of electrophoretic mobilities within a given electrophoresis chamber.

Still another means to achieve the hydrodynamic compensation for the system of this invention is to employ means connected to at least a portion of the plurality of individual collection tubes at the outlet manifold of the electrophoresis chamber such that increased flow could be induced within the outlet tubes closer to the sides of the electrophoresis chamber, thereby again reducing the distortion forces which produce the crescent distortion effect.

The hydrodynamic compensation concept is illustrated in FIG. 5. FIG. 5 can be best understood by reference to the previous FIG. 4 wherein the three separate conditions possible within an electrophoresis chamber are illustrated, namely a crescent opening to the left 52, an undistorted circular cross section 54, and a cross section with a crescent opening to the right 56. Referring now to FIG. 5, it is evident that introducing an additional lateral flow out through each side of the electrophoresis chamber will compensate for the undesirable distortions found in 52 and 56 of FIG. 4. The compensation is achieved by the super-position of the flow vectors 64 and 66 upon the flow vectors normally present within the chamber as shown in FIG. 4. If these added hydrodynamic compensation flows were equal, the lateral velocity profile at the center of the chamber would be unchanged. Therefore, a particle stream near the center of the chamber 54 would retain its original circular cross section 60. For the sample on the left of lower mobility 52, the added velocity component at the center line due to flow through the left porous membrane removes the excess deflection due to the electro-osmotic return flow, thereby creating a circular sample across section 58. For the sample on the right of higher mobility 56, the added velocity component of the center line due to flow through the right hand membrane adds to the deflection due to the electro-osmotic return flow, thereby, producing a circular cross section for this sample 62 as well. The mobility of the sample components 59 is shown in FIG. 5 as increasing to the right in a manner similar to previous FIGS. 4, 3, and 2.

As mentioned above, the porous membranes can also be utilized to introduce a uniform flow across the chamber to compensate for distortion within a single sample. For example, if the membrane area and porosity are uniform along the length of the chamber, then a constant pressure differential between one of the electrode chambers and the electrophoresis chamber and an equal differential between the electrophoresis chamber and the other electrode chamber would result in a uniform lateral flow across the chamber, which, in addition to the electro-osmotic flow inherent to the wall material used, would compensate for the crescent distortion in a sample stream of a single electrophoretic mobility.

Figures 6, 7, 8:
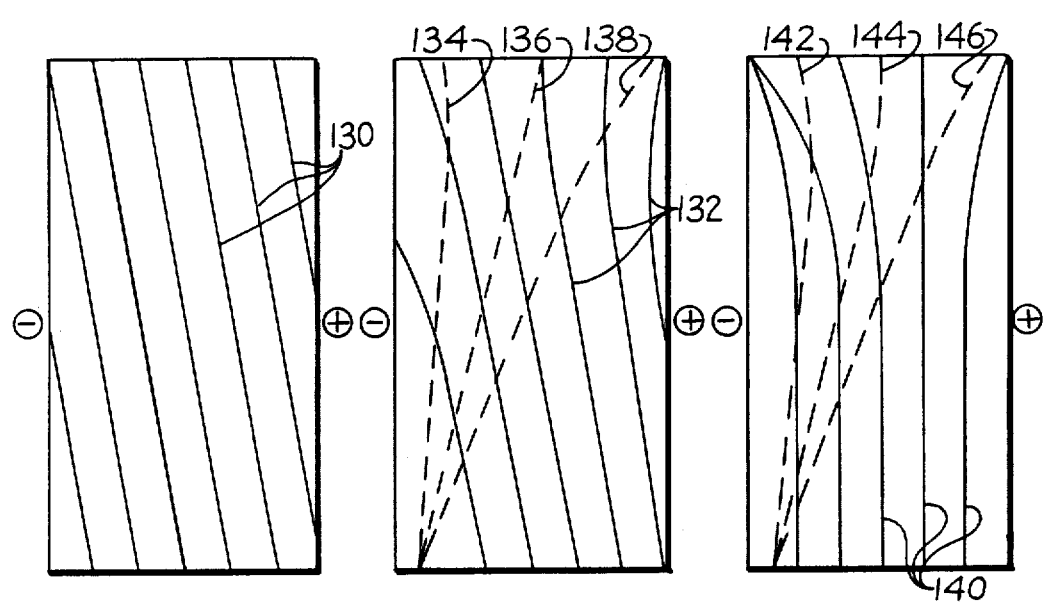
FIG. 6 illustrates the flow lines at mid-chamber for uniform hydrodynamic compensation.
FIG. 7 illustrates the flow lines at mid-chamber for an appropriate non-uniform hydrodynamic compensation, implemented by the porous membranes.
FIG. 8 illustrates the flow lines at mid-chamber for an appropriate non-uniform hydrodynamic compensation implemented by the outlet tubes of the chamber.

The streamlines 130 at the chamber mid-plane for the resulting flow are illustrated by FIG. 6.

To compensate for the crescent distortion of streams of different mobility, the lateral velocity across the chamber must be made to be non-uniform. If the crescent distortion of a stream of a given electrophoretic mobility is compensated for by the flow shown in FIG. 6, then an additional lateral component as indicated by 58 is required to compensate for a stream of lower mobility; and an additional lateral component as indicated by 62 is required for streams of higher mobility. This could be effected by increasing the membrane area porosity, or pressure differential, near the outlet on the cathode side and decreasing the membrane area, porosity, or pressure differential near the outlet on the anode side. The streamlines 132 at the chamber mid-plane of the resulting flow are illustrated by FIG. 7. The paths taken by particle streams of low 134, medium 136, and high 138 mobility are shown by the dotted lines; and for these paths, the amount of compensation can be seen to vary with the magnitude of mobility in the desired manner.

A similar variation in the amount of compensation vis-a-vis the magnitude of sample stream moblity can be affected by controlling the flowrates through outlet tubes on either side of the sample. For example, if the flow was increased by unequal amounts for the outlet tubes at the ends of the array, the resulting streamlines at the chamber mid-plane could appear as in FIG. 8. Here again, the paths taken by particle streams of low 142, medium 144, and high 146 mobility are shown by the dotted lines. If the chamber flow is pressure-referenced to the ambient barometric pressure at the ends of the outlet tubes, then the flow through any given outlet tube can be increased by decreasing the geopotential altitude of the end of that tube relative to the other tubes.

Figure 9:
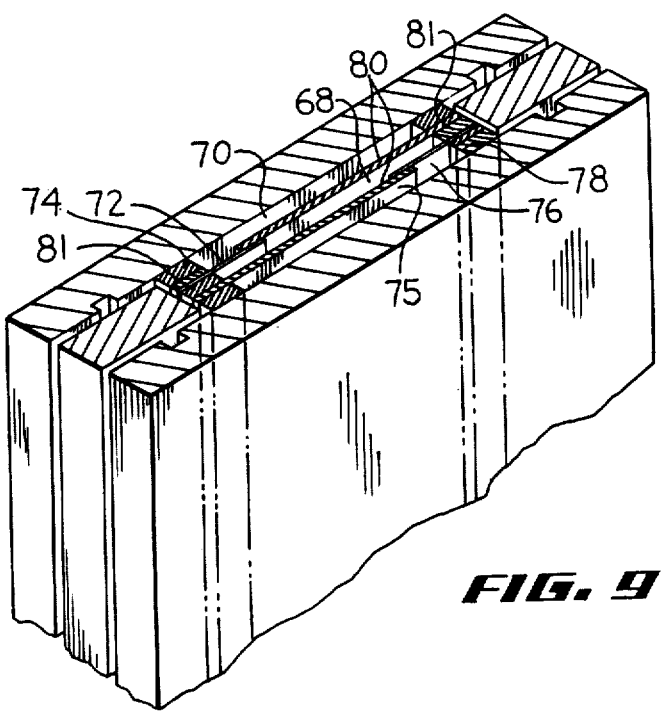
FIG. 9 is a cut-away isometric view of the apparatus of this invention.

FIG. 9 is a cross sectional isometric view of one configuration of the system of this invention. The electrophoresis chamber itself 68 is found in the center of the apparatus and is bounded by the two flat parallel rectilinear plates 80. In this configuration there is a small gap along one lateral edge of each of the flat elongate parallel plates such that each gap is found at the side of the chamber opposite to the gap of the other plate. These gaps are covered by the membranes 72 and 75 which serve to separate the electrophoresis chamber 80 from the electrode chambers 70 and 75 which also serve as cooling means for the electrophoresis chamber. Electrodes 74 and 78 are disposed parallel and immediately adjacent to the porous membranes such that ions may be produced and then migrated through the membranes into the electrophoresis chamber as the result of the electrical field set up between the two electrodes 74 and 78. It is the action of this electrical field that induces the electrophoretic motion to the sample streams within the chamber.

Figure 10:
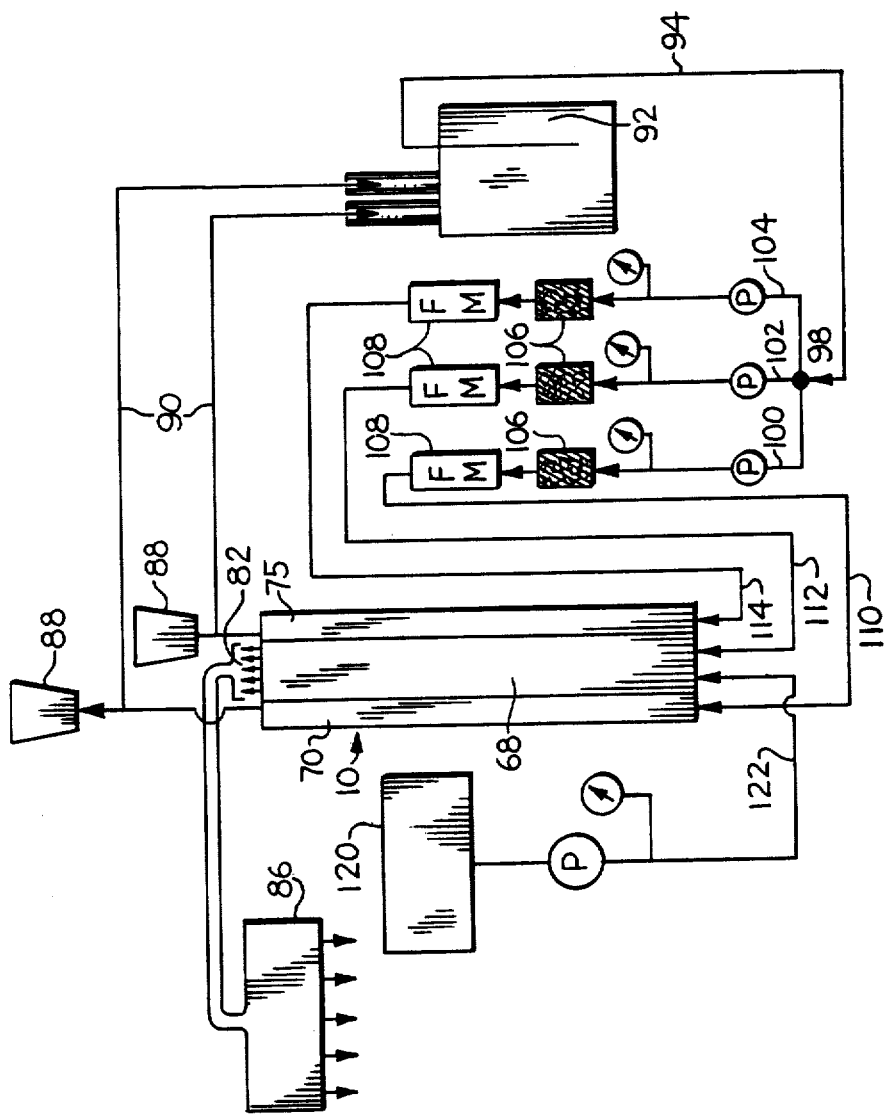
FIG. 10 is a schematic diagram of an electrophoresis separation chamber and its supporting equipment.

FIG. 10 is a schematic functional diagram of the electrophoresis process. The electrophoresis device 10 comprises the electrophoresis chamber itself 68 and the electrode chambers 70 and 75. The outlet manifold 82 for the electrophoresis chamber 68 is composed of a plurality of tubes, often more than 100 separate tubes, which are connected to collection means 86 wherein each of the various sample streams is collected. The flow through the outlet tubes can be controlled either by pumping the tubes individually or by using small bore tubing that tends to allow flow differences inversely proportional to length differences when a constant pressure difference is effected between its inlets and outlets. The flow through any given tube can also be increased by decreasing the geopotential height of its outlet relative to the outlets of the other tubes, which has the effect of increasing the pressure differential across that tube. Any of these means can be used in order that some of the outlet tubes may have their flows controllably varied such that the outlet tubes closer to the sides of the electrophoresis chamber may have increased flow rates compared to those closer to the center of the electrophoresis chamber such that the hydrodynamic compensation effects may be introduced to the fluid sample streams in the vicinity of the collection manifold 82.

The buffer solutions from each of the electrode chambers 70 and 75 are drawn off through electrolysis product gas traps 88 along through conduit means 90 to a buffer reservoir 92. The ends of the small diameter conduits 90 used for electrode buffer returns exit into the large conduits 96 leading to the buffer reservoir 92. Since the small diameter tubes 90 are filled with buffer solution, they have a syphon effect, and their outlets are the atmospheric pressure references for the electrode buffer flow circuits. Therefore, the pressures in each circuit can be controlled by varying the geopotential height of the exits for each of the tubes 90 within the syphon break tubes 96. Decreasing the height of the exit will decrease pressure, and increasing exit height will increase pressure. Since the pressure within the chamber is controlled by the geopotential height of its outlet tube exits, the pressure differentials across the membranes can be controlled by changing the geopotential heights of the electrode buffer tube exits. The same effect could also be achieved by the use of throttling valves, not shown, in the electrode buffer conduits 90.

Buffer is then drawn off from the reservoir 92 through a conduit 94 to a three-way junction 98 feeding into a conduit supplying cathode electrode chamber 100, a conduit supplying the electrophoresis chamber 102, and a conduit supplying the anode electrode chamber 104. Each of these three conduits is then connected to appropriate filters 106 and flow meters 108 and is finally connected to the electrophoresis device 10 itself by conduits 110, 112 and 114 respectively. Conduit 112 supplying the electrophoresis chamber 68 is commonly connected therewith by an inlet manifold not shown such that uniform flow conditions exist at the inlet to the electrophoresis chamber 68. The sample which is desired to be separated is contained within a sample reservoir 120 and is introduced into the electrophoresis chamber 68 by a conduit 122 through a sample inlet port, not shown. The sample inlet port is commonly located at a small distance downstream from the inlet manifold. Cooling systems are employed with electrophoresis systems to remove the heat introduced by Joule heating within the chamber and to reduce the resulting distortion effects produced by convection cells within the chamber. These means are not shown herein but are well known to those with a skill in the art.

I claim as my invention:

1. In an electrophoresis separation process conducted with an apparatus comprising:

a lengthwise elongate rectangular buffer filled separation chamber defined by two elongate spaced apart parallel plates forming a front and a back to the chamber, two sides, an end comprising a collection manifold having a plurality of spaced apart collection tubes, an end comprising a buffer solution inlet manifold assembly;

two buffer filled electrode chambers, each disposed adjacent to one of the sides of the chamber and separated therefrom by a porous membrane;

at least one sample inlet port located at or near the inlet of the chamber;

the improvement comprising controllably varying flow within the apparatus laterally across the chamber such that crescent distortion for at least one of a plurality of individual components of a sample introduced through the sample inlet port is minimized.

2. The process of claim 1 wherein the flow is controllably varied by inducing a flow from the separation chamber into at least one of the electrode chambers through the corresponding porous membrane.

3. The process of claim 1 wherein the flow is controllably varied by inducing increased flow out through at least one of the outlet tubes proximate at least one of the sides of the chamber.

4. The process of claim 1 wherein the flow is controllably varied such that a substantially uniform lateral flow is induced within the chamber.

5. The process of claim 1 wherein the flow is controllably varied such that a substantially nonuniform lateral flow is induced within the chamber.

* * * * *